(12) United States Patent
Edman et al.

(10) Patent No.: US 7,227,631 B2
(45) Date of Patent: Jun. 5, 2007

(54) METHOD FOR EXAMINING A TEST SAMPLE BY MEANS OF FLUORESCENCE SPECTROSCOPY, ESPECIALLY FLUORESCENCE CORRELATIN SPECTROSCOPY, AND DEVICE FOR CARRYING OUT SAID METHOD

(75) Inventors: Lars Edman, Stockholm (SE); Rudolf Rigler, Danderyd (SE)

(73) Assignee: Evotec Technologies GmbH, Duesseldorf (DE)

( * ) Notice: Subject to any disclaimer, the term of this patent is extended or adjusted under 35 U.S.C. 154(b) by 648 days.

(21) Appl. No.: 10/470,246

(22) PCT Filed: Jan. 25, 2002

(86) PCT No.: PCT/EP02/00797

§ 371 (c)(1),
(2), (4) Date: Jan. 16, 2004

(87) PCT Pub. No.: WO02/059582

PCT Pub. Date: Aug. 1, 2002

(65) Prior Publication Data

US 2004/0144929 A1 Jul. 29, 2004

(30) Foreign Application Priority Data

Jan. 25, 2001 (DE) ................ 101 03 304

(51) Int. Cl.
*G01N 21/01* (2006.01)
(52) U.S. Cl. ................................. 356/244
(58) Field of Classification Search ............ None
See application file for complete search history.

(56) References Cited

U.S. PATENT DOCUMENTS

2003/0015425 A1* 1/2003 Bohm et al. ............. 204/453
2003/0146091 A1* 8/2003 Vogel et al. .......... 204/403.01

FOREIGN PATENT DOCUMENTS

DE 195 08 366 A 9/1996
EP 0 679 251 A 11/1995

OTHER PUBLICATIONS

Eigen M et al., "Sorting Single Molecules: Application to Diagnostics and Evolutionary Biotechnology", Proceedings of the National Academy of Sciences of USA, National Academy of Scince, Washington, U.S., 1994, vol. 91, pp. 5740-5747, XP-002029412.

* cited by examiner

*Primary Examiner*—Michael P. Stafira
(74) *Attorney, Agent, or Firm*—Rothwell, Figg, Ernst & Manbeck, P.C.

(57) ABSTRACT

In a method for the fluorescence spectroscopic, in particular fluorescence correlation spectroscopic study of a measurement sample, the latter is introduced into a sample holding chamber (12) formed hollowed in a sample support (10). Electrically charged analytes contained in the measurement sample are then concentrated in a measurement volume (26) lying inside the sample volume, whereupon the measurement volume (26) is studied. According to the invention, the boundary walls (28) of the sample holding chamber (12) are brought essentially surface-wide to an electrostatic potential having the same sign as the charge of the analytes in order to concentrate the analytes in the measurement volume (26). An electrical molecule trap formed in this way can be produced very straightforwardly and is suitable in particular for screening studies of measurement samples, a large multiplicity of which are arranged close together in indentations (12) of the sample support (10).

5 Claims, 2 Drawing Sheets

Figure 1:
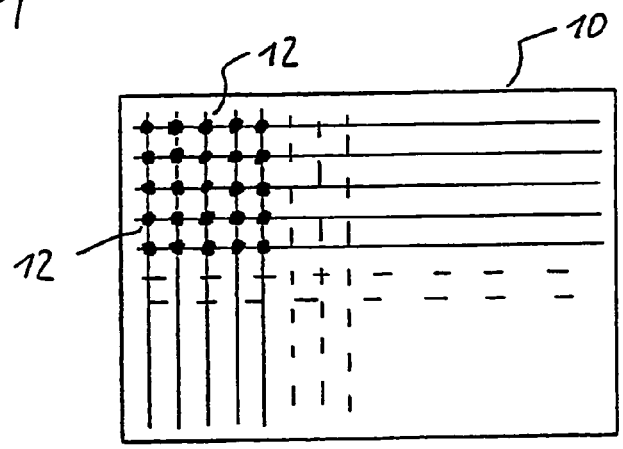

METHOD FOR EXAMINING A TEST SAMPLE BY MEANS OF FLUORESCENCE SPECTROSCOPY, ESPECIALLY FLUORESCENCE CORRELATIN SPECTROSCOPY, AND DEVICE FOR CARRYING OUT SAID METHOD

CROSS REFERENCE TO RELATED APPLICATION

This application is a 35 USC § 371 National Phase Entry Application from PCT/EP02/00797, filed Jan. 25, 2002, and designating the U.S.

The invention relates to the fluorescence spectroscopic, in particular fluorescence correlation spectroscopic study of a measurement sample.

Fluorescence spectroscopy can be used in order to detect the presence of specific analytes in a measurement sample, for example a biological sample, e.g. a bodily fluid such as blood, serum, plasma, urine, saliva etc, or a molecular biological reaction batch, e.g. a sequencing batch. The analytes may be substances with a low molecular weight, such as medicinal preparations, hormones, nucleotides, metabolics etc., or substances with a high molecular weight, such as proteins, sugars, nucleic acids etc., viruses or cells, such as bacterial cells, and other substances. In order to be able to identify the relevant analytes, they are labeled with reagents which carry fluorophores and emit fluorescence signals when exposed to light, in particular laser light, these signals being detected and evaluated. In fluorescence correlation spectroscopy, auto- and/or cross-correlations of the detected fluorescence signals are then evaluated. Further information about fluorescence spectroscopy and, in particular, about fluorescence correlation spectroscopy can be found, for example, in EP 0 679 251 B1.

Only a small sub-volume of the sample—the measurement volume—normally lies at the focus of the microscope being used for the study. In order to prevent bleaching of the fluorescent molecules by excessively intense and prolonged exposure to light, and vitiation of the measurement results, efforts are made to make the measurement volume ultra-small, for example in the femtolitre range. If the analytes to be identified are only present at a low concentration in the measurement sample, however, with such small measurement volumes it may take a comparatively long time, and even an unacceptably long time in the case of large-scale screening studies, for one of the intended analytes to diffuse into the measurement volume and therefore become observable.

In order to accelerate the measurement, therefore, electrical molecule traps are proposed in the specialist literature and, inter alia, in the aforementioned European specification EP 0 679 251 B1, by means of which the analytes to be detected, if they are electrically charged, can be driven into the measurement volume and concentrated there under the effect of electrical fields. EP 0 679 251 B1 discloses, for example, that the intended analytes may be kept in the measurement volume by means of a rotating AC electrical field. Transversely to this alternating field, they are prevented from leaving the measurement volume by two poles electrically charged with the same sign. In DE 195 08 366 C2, it is proposed to generate an electrical field between an annular electrode and a capillary arranged with its tip at the centre of the annular electrode, which electrical field causes the intended analytes to become concentrated around the capillary tip.

Not only because of the space requirement of the electrodes needed for generating the electrical fields, but also because of the outlay often required for the electrical control of the electrodes, such molecule traps per se are primarily suitable for individual studies. However, they prove to be less suitable when a large number of measurement samples, for example from several thousand up to a few hundred thousand, which are arranged in closely neighboring indentations of a common sample support (for example a multi-well film known from EP 0 679 251 B1), are intended to be studied with acceptable outlay in the scope of screening studies.

It is therefore an object of the invention to provide a more straightforward way of electrically concentrating analytes.

To achieve this object, the invention is based on a method for the fluorescence spectroscopic, in particular fluorescence correlation spectroscopic study of a measurement sample, in which method the measurement sample is introduced into a sample holding chamber formed hollowed in a sample support, then electrically charged analytes contained in the measurement sample are concentrated in a measurement volume lying inside the sample volume and the measurement volume is studied.

In this method, it is proposed according to the invention that the boundary wall of the sample holding chamber be brought essentially surface-wide to an electrostatic potential having the same sign as the charge of the analytes in order to concentrate the analytes in the measurement volume. Owing to the electrical charge applied to the boundary walls of the sample holding chamber, repulsion forces are exerted on the analytes in the measurement sample which are charged with the same sign. If the sample holding chamber is configured suitably, the effect of this repulsion is that the analytes move toward the measurement volume in a controlled way and accumulate there. It has been shown that in this way, analytes whose concentration in the measurement sample lies below the nM range down to the aM range can readily be enriched to values in the nM range in the measurement volume, so that the presence of these analytes can be detected within acceptable measurement times (for example in less than one second).

When a charge sign of the analytes is referred to here, with respect to which the wall potential of the sample holding chamber is intended to have the same sign, it should be understood that this means the charge sign of the fluorophore-labeled analytes, since it is these which are intended to be concentrated in the measurement volume.

The solution according to the invention does not require any complicated electrode arrangement taking up a great deal of space. Instead, the walls of the sample holding chamber are themselves used as electrodes. A single charge application may be sufficient for charging these walls electrostatically; the chamber walls can generally hold the charge without special extra measures, at least for the measurement time. It is, however, also conceivable for the chamber walls to be constantly connected to a potential source throughout the measurement time. Neither is any control of the potential of the chamber walls necessary. The method according to the invention makes it possible to trap the analytes reliably in the measurement volume, without having to vary the potential of the chamber walls dynamically by feedback. A time-invariant wall potential is not even necessary. It merely needs to be high enough for sufficiently strong repulsion forces to be generated in order to achieve the intended concentration of the analytes. Possible charge leakage from the chamber walls may therefore be tolerable so long as the basic level of the wall potential is high enough.

According to a further aspect, the invention relates to a device for carrying out the aforementioned method. This device comprises a sample support with at least one sample holding chamber formed hollowed in it, as well as means for essentially surface-wide electrostatic charging of the boundary walls of the sample holding chamber.

The sample holding chamber may be designed so that it is undercut. This can help to keep a point of Coulomb force equilibrium inside the volume of the measurement sample. It is not, however, fundamentally necessary to have such an equilibrium point inside the volume of the measurement sample. It is conceivable for a point of force equilibrium to lie only above the filling level, up to which the sample holding chamber is filled with the measurement sample. It is even envisageable for the sample holding chamber to be configured in such a way that no point of Coulomb force equilibrium exists at all. Since the repulsion forces drive the analytes in the direction of lower electrostatic potentials, it is merely necessary to make sure that the measurement volume lies in a region of lowest electrostatic potential inside the overall volume of the measurement sample. For this reason, a sample holding chamber free of undercuts may be used.

In order to make the procedure of electrostatically charging the chamber walls as economical as possible for screening studies, the sample support may have a multiplicity of preferably matricially arranged sample holding chambers, the boundary walls of which can be electrostatically charged together. It is, however, clear that a sample support with a multiplicity of sample holding chambers, at least some of whose chamber walls can be electrostatically charged individually, may also be used.

An exemplary embodiment of the invention will be explained in more detail with reference to the appended drawings, in which:

FIG. 1 schematically shows a plan view of a sample support, and

Figure 2:
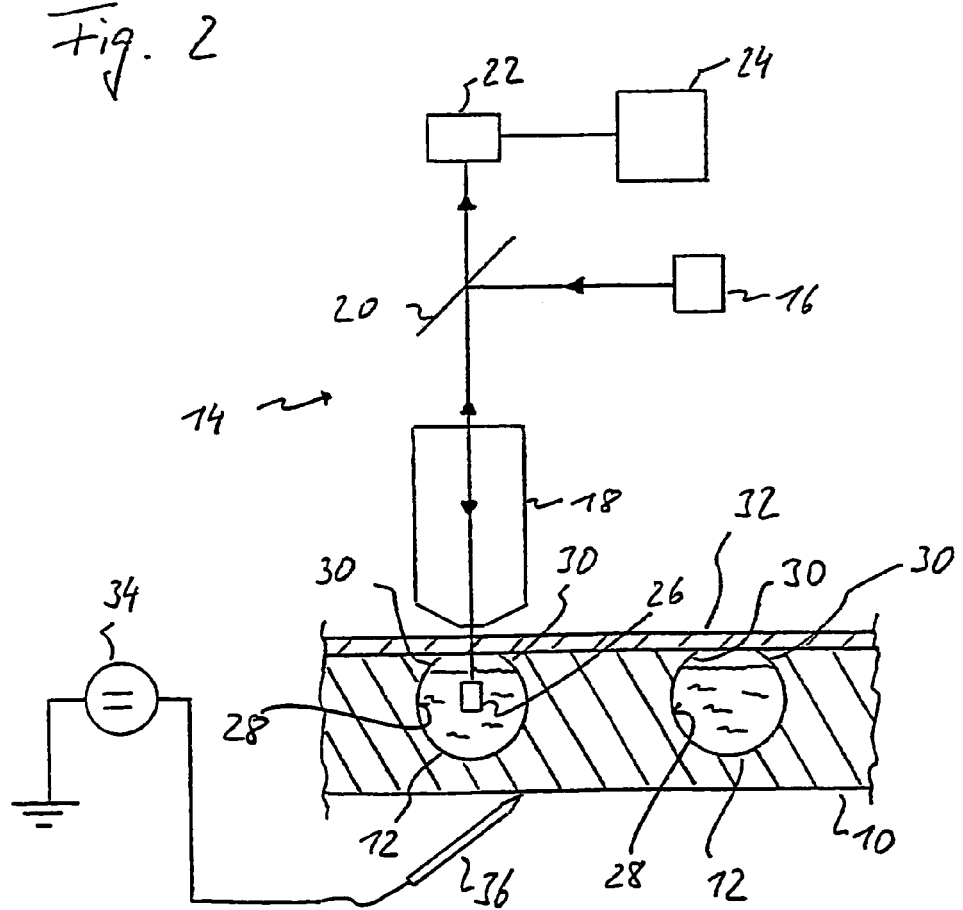

FIG. 2 schematically shows a measurement arrangement for studying a measurement sample, which is located in a sample holding chamber of the sample support.

Figure 3:
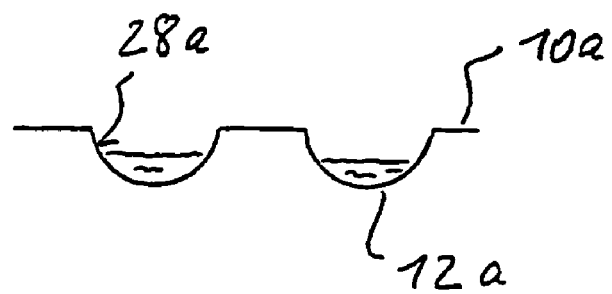

FIG. 3 is another embodiment of the sample holding chambers of FIG. 2.

The flat sample support shown in FIG. 1, where it is denoted by 10, has a multiplicity of sample holding chambers 12 indicated by black dots in a matrix arrangement, which may be filled with blood samples or samples of other solutions that are to be studied with regard to the presence of specific viruses, DNA fragments or other analytes. The sample holding chambers 12 are formed by indentations or hollows in the sample support 10.

The size of the sample holding chambers 12 will be selected according to the intended use of the relevant sample support 10. For example, the volume of each sample holding chamber 12 may lie between 100 fl and 100 µl. The range of sample holding chambers 12 to be accommodated per unit area of the sample support 10 is correspondingly large. Between 100 and 100,000 sample holding chambers 12 may readily be accommodated per cm$^2$ of the sample support 10. The sample, support 10 may, for example, be made of a film material. It may, however, also be designed as a plate part.

In the scope of a screening study of measurement samples from different patients, for example, one column of the matrix of sample holding chambers 12 may be reserved for each patient. The measurement samples with which the sample holding chambers 12 are filled will then be mixed with different test solutions on each row. Each test solution will then contain different analyte-specific reagents, which are labeled with fluorescent dyes. It is hence possible to detect different analytes from row to row.

The measurement arrangement shown in FIG. 2 is used for fluorescence spectroscopic study of the measurement samples. It comprises a microscope arrangement denoted overall by 14, with a laser source 16, a lens 18, a dichroic mirror 20, a photodetector 22 and an evaluation unit 24. The laser beam provided by the laser source 16 is fed via the mirror 20 into the lens 18, and focused by the latter onto a small volume element indicated at 26 inside the volume of the measurement sample, with which the relevant sample holding chamber 12 is filled. By means of the lens 18 and optionally a diaphragm, which is not represented in detail, this volume element 26 is imaged confocally onto the detector 22. The laser beam stimulates the fluorophores located (freely or bound to the intended analytes) in the volume element 26 to fluoresce. The light pulses thereby generated are registered by the detector 22 and evaluated in the evaluation unit 24. The detection of the intended analytes is preferably carried out here using auto- and/or cross-correlations of the fluorescence signals delivered by the detector 22.

Confocal microscope arrangements of this type are known per se. For example, reference is made to EP 0 679 251 B1 in which details of such a microscope can be found. It is clear that the microscope arrangement 14 may also have two or more detectors 22 for recording different fluorescence wavelengths. It may also be designed as a dual microscope with two lenses 18, one arranged on each side of the sample support 10, so long as the sample support 10 consists of an optically transparent material. Such a dual microscope can also be found in EP 0 679 251 B1.

In order to increase the concentration of the analytes to be detected in the volume element 26, and therefore to shorten the measurement time, the inner wall (denoted by 28) of the relevant sample holding chamber 12 is charged surface-wide to an electrostatic potential which has the same sign (positive or negative) as the electrical charge of the intended analytes. DNA strands, for example, are usually negatively charged; the chamber inner wall 28 will therefore be negatively charged in this case. The electrical charge carriers attracted onto the chamber inner wall 28 by the charging exert Coulomb repulsion forces on all molecules and other particles in the measurement sample which are charged with the same sign, and therefore also on the intended analytes. These repulsion forces drive the analytes, along the potential gradient prevailing in the sample holding chamber 12, to regions of lower electrostatic potential. The analytes finally accumulate in the region which has the lowest electrostatic potential inside the measurement sample volume. A particularly steep potential gradient, and therefore a particularly effective and fast concentration process, is obtained if the vectorially added repulsion forces being exerted by the charge carriers distributed over the chamber inner wall 28 mutually cancel out at the place whose electrostatic potential inside the measurement sample volume is lowest, so that there is a Coulomb force equilibrium at this position.

In order to have a point of such force equilibrium existing inside the sample holding chamber 12, and preferably even inside the measurement sample volume, the sample holding chambers 12 may be designed with an undercut. In this design, the edge regions (denoted by 30) of the openings partially overhang or overlap the sample holding chambers 12, as can be seen clearly in FIG. 2. Repulsion forces with a component directed at the bottom of the sample holding chamber 12 are created in these edge regions 30 when the chamber inner wall 28 is electrostatically charged, and they counteract the repulsion forces directed out from the sample holding chamber 12, hence making it possible to establish a force equilibrium inside the sample holding chamber 12.

Force components directed at the chamber bottom may also, for example, be generated by electrostatically charging a cover element 32, preferably a cover film, by means of which the openings of the sample holding chambers 12 can be covered.

If no point of force equilibrium exists inside the measurement sample volume (either because such a point only exists outside the measurement sample volume or because it does not exist at all), then the repulsion forces provide concentration of the analytes to be detected in a region close to the surface of the measurement sample. For this reason, it is readily possible to use sample holding chambers 12a free of undercuts, as shown by way of example in FIG. 3. The same elements as in FIG. 2 are provided with the same references there, but suffixed with a lower case letter.

The electrostatic charging of the chamber inner walls 28 of the sample holding chambers 12 may, for example, be carried out by means of an electrode 36 which is connected to a DC voltage source 34 and is brought in contact with the sample support 10. If the sample support 10 is made of an electrically conductive material, the electrode 36 may make contact with the sample support 10 at any position. In this case, all the sample holding chambers 12 could be charged together at the same time. However, it is also envisageable for the sample support 10 to consist of a non-Conductive base material, while the sample holding chambers 12 are coated with a conductive material on the inside. In this way, the sample holding chambers 12 could be charged individually.

The electrical potential, relative to ground potential, for charging the chamber inner walls 28 depends on the dimensions of the sample holding chambers 12 and on the level of the intended concentration gradient of the relevant analytes in the sample holding chamber 12. The range of potential differences suitable for use may readily lie between 10 V and 10,000 V.

The invention claimed is:

1. A method for the fluorescence spectroscopic, in particular fluorescence correlation spectroscopic study of a measurement sample, in which method the measurement sample is introduced into a sample holding chamber (12) formed hollowed in a sample support (10), electrically charged analytes contained in the measurement sample are concentrated in a measurement volume (26) lying inside the sample volume and the measurement volume (26) is studied, characterized in that the boundary walls (28) of the sample holding chamber (12) are brought essentially surface-wide to an electrostatic potential having the same sign as the charge of the analytes in order to concentrate the analytes in the measurement volume (26).

2. A device for carrying out the method as claimed in claim 1, characterized by a sample support (10) with at least one sample holding chamber (12) formed hollowed in it, as well as means (34, 36) for essentially surface-wide electrostatic charging of the boundary walls (28) of the sample holding chamber (12).

3. The device as claimed in claim 2, characterized in that the sample holding chamber (12) is undercut.

4. The device as claimed in claim 2, characterized in that the sample holding chamber (12) is free of undercuts.

5. The device as claimed in claim 2, characterized in that the sample support (10) has a multiplicity of preferably matricially arranged sample holding chambers (12), the boundary walls (28) of which can be electrostatically charged together.

* * * * *